US00PP34007P3

(12) United States Plant Patent
Meulenbroek

(10) Patent No.: US PP34,007 P3
(45) Date of Patent: Mar. 15, 2022

(54) STRAWBERRY PLANT NAMED 'TWIST'

(50) Latin Name: ***Fragaria* x *ananassa***
Varietal Denomination: Twist

(71) Applicant: FRESH FORWARD HOLDING B.V., Eck en Wiel (NL)

(72) Inventor: Egbertus Joseph Meulenbroek, Zetten (NL)

(73) Assignee: FRESH FORWARD HOLDING B.V., Eck en Wiel (NL)

( * ) Notice: Subject to any disclaimer, the term of this patent is extended or adjusted under 35 U.S.C. 154(b) by 0 days.

(21) Appl. No.: 17/324,506

(22) Filed: May 19, 2021

(65) Prior Publication Data

US 2021/0368663 P1 Nov. 25, 2021

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./156, 208, 209
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of Strawberry plant named 'Twist', characterized by its compact and upright plant habit; moderately vigorous growth habit and rapid growth rate; early flowering habit; early and uniform fruit ripening; large conical fruits that are glossy and reddish orange in color; pleasant fruit aroma and sweet taste; and excellent fruit postharvest longevity.

3 Drawing Sheets

Figure 1:
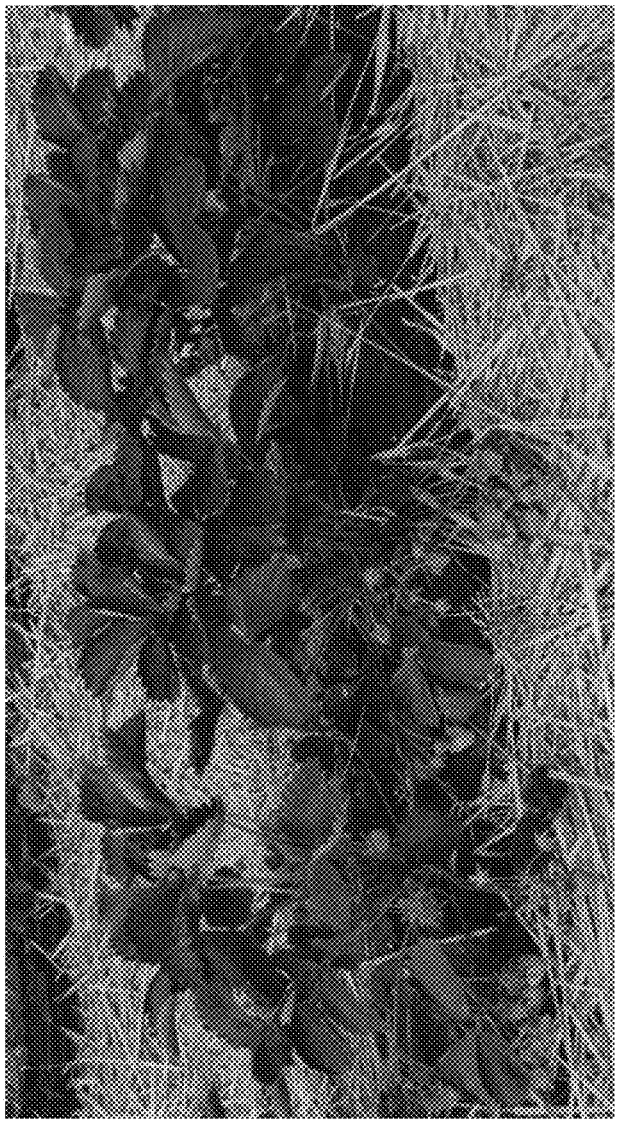

Botanical designation: *Fragaria* x *ananassa.*
Cultivar denomination: 'TWIST'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Fresh Forward Holding B.V. of Eck en Wiel, The Netherlands on May 20, 2020, application number 2020/1263. Foreign priority is claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present Invention relates to a new and distinct cultivar of Strawberry plant, botanically known as *Fragaria* x *ananassa* and hereinafter referred to by the name 'Twist'.

The new Strawberry plant is a product of a planned breeding program conducted by the Inventor in Eck en Wiel, The Netherlands. The objective of the breeding program was to develop new Strawberry plants with good fruit quality, ease of harvesting, high yield, large attractive fruits and good postharvest longevity.

The new Strawberry plant originated from a cross-pollination by the Inventor in March, 2013 in Eck en Wiel, The Netherlands of a proprietary selection of *Fragaria* x *ananassa* identified as code number E2008-001, not patented, as the female, or seed, parent with a proprietary selection of *Fragaria* x *ananassa* identified as code number E2010-411, not patented, as the male, or pollen, parent. The new Strawberry plant was discovered and selected by the Inventor as a single plant from within the progeny of the stated cross-pollination in a controlled environment in Eck en Wiel, The Netherlands in June, 2015.

Asexual reproduction of the new Strawberry plant by runner cuttings in a controlled environment at Eck en Wiel, The Netherlands since September, 2015 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Twist'. These characteristics in combination distinguish 'Twist' as a new and distinct Strawberry plant:

1. Compact and upright plant habit.
2. Moderately vigorous growth habit and rapid growth rate.
3. Early flowering habit.
4. Early and uniform fruit ripening.
5. Large conical fruits that are glossy and reddish orange in color.
6. Pleasant fruit aroma and sweet taste.
7. Excellent fruit postharvest longevity.

Plants of the new Strawberry differ primarily from plants of the female parent selection in the following characteristics:

1. Plants of the new Strawberry are more upright than plants of the female parent selection.
2. Fruits of plants of the new Strawberry are conical in shape whereas fruits of plants of the female parent selection are cylindrical to rhomboidal in shape.
3. With relation to their position to the fruits, sepals of plants of the new Strawberry are positioned outwardly whereas sepals of plants of the female parent selection are positioned more upright.

Plants of the new Strawberry differ primarily from plants of the male parent selection in the following characteristics:

1. Plants of the new Strawberry are more upright than plants of the male parent selection.
2. Fruits of plants of the new Strawberry are conical in shape whereas fruits of plants of the male parent selection are cylindrical to rhomboidal in shape.
3. With relation to their position to the fruits, sepals of plants of the new Strawberry are positioned outwardly whereas sepals of plants of the male parent selection are positioned more upright.

Plants of the new Strawberry can be compared to plants of *Fragaria* L. 'Flair', disclosed in U.S. Plant Pat. No. 23,162. In side-by-side comparisons, plants of the new Strawberry differ primarily from plants of 'Flair' in the following characteristics:

1. Plants of the new Strawberry are stronger and more vigorous than plants of 'Flair'.
2. Flower peduncles of plants of the new Strawberry are longer than flower peduncles of plants of 'Flair'.
3. Fruits of plants of the new Strawberry are lighter red in color than fruits of plants of 'Flair'.
4. Fruits of plants of the new Strawberry are conical in shape whereas fruits of plants of 'Flair' are long conical to rounded cordate in shape.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet (FIG. 1) is a side perspective view of typical fruiting plants of 'Twist' grown in a greenhouse environment.

Figure 2:
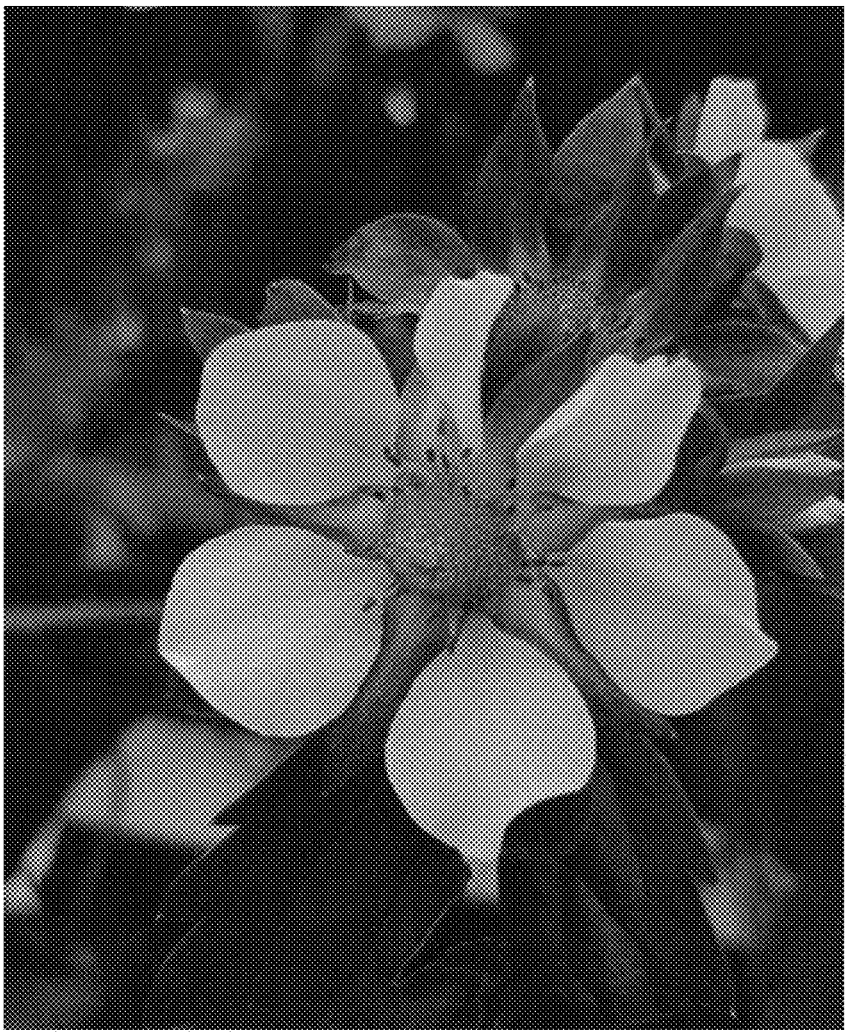

The photograph on the second sheet (FIG. 2) is a close-up view of typical flowers of plants of 'Twist'.

Figure 3:
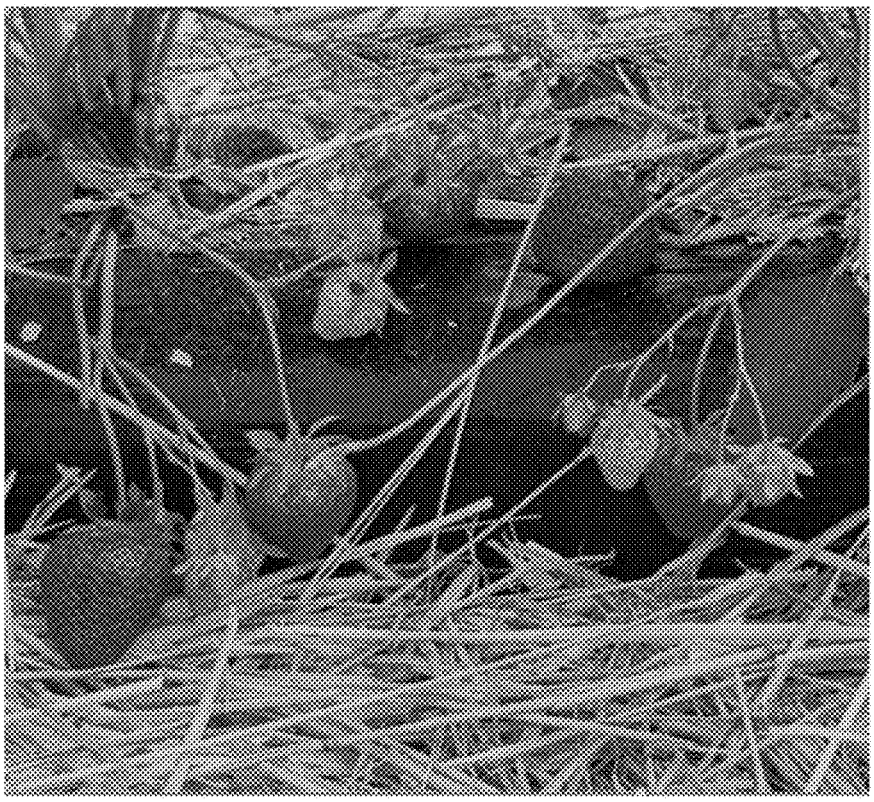

The photograph on the third sheet (FIG. 3) is a close-up view of typical developing and developed fruits of plants of 'Twist'.

DETAILED BOTANICAL DESCRIPTION

The following observations and measurements describe plants grown in beds and plants grown in 2.5-liter containers with two plants per container during the winter and spring in a glass-covered greenhouse in Huissen, The Netherlands and under cultural practices typical of commercial Strawberry production. During the production of the plants, day temperatures ranged from 10° C. to 25° C. and night temperatures ranged from 8° C. to 12° C. Plants were one year old when the photographs and the description were taken. In the following description, color references are made to The Royal Horticultural Society Colour Chart, 2001 Edition, except where general terms of ordinary dictionary significance are used.

Botanical classification: *Fragaria* x *ananassa* 'Twist'.

Parentage:

*Female, or seed, parent.*—Proprietary selection of *Fragaria* x *ananassa* identified as code designation E2008-001, not patented.

*Male, or pollen, parent.*—Proprietary selection of *Fragaria* x *ananassa* identified as code designation E2010-411, not patented.

Propagation:

*Type.*—By runner cuttings.

*Time to initiate roots, summer.*—About one to four days at soil temperatures about 15° C. and ambient temperatures about 17° C.

*Time to produce a rooted young plant, summer.*—About two to three weeks at soil temperatures about 15° C. to 20° C. and ambient temperatures about 17° C.

*Root description.*—Medium in thickness, fibrous; typically cream to white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Perennial; compact, upright plant habit; leaves basal; moderately vigorous growth habit; rapid growth rate; density of foliage, medium.

*Plant height.*—About 30 cm to 35 cm.

*Plant diameter.*—About 35 cm to 40 cm.

*Stolon texture.*—Sparsely pubescent.

*Stolon color.*—Close to 144A.

Leaf description:

*Arrangement and appearance.*—Basal rosette; compound with typically three leaflets per leaf; leaflets are not variegated and typically without anthocyanin when grown under normal and healthy growing conditions; blistering has not been observed.

*Leaflet length.*—About 12 cm to 15 cm.

*Leaflet width.*—About 9 cm to 14 cm.

*Leaflet shape.*—Broadly ovate; terminal leaflet concave in cross-section.

*Leaflet apex.*—Obtuse to acute.

*Leaflet base.*—Attenuate to obtuse.

*Leaflet margin.*—Serrate.

*Leaflet texture and luster, upper surface.*—Pubescent; slightly glossy.

*Leaflet texture and luster, lower surface.*—Pubescent; matte.

*Leaflet venation.*—Pinnate.

*Leaflet color.*—Developing leaflets, upper surface: Close to 137A. Developing leaflets, lower surface: Close to 138A. Fully expanded leaflets, upper surface: Close to between 137A and 139A; venation, close to 144C. Fully expanded leaflets, lower surface: Close to 138A; venation, close to 144C.

*Petioles.*—Length: About 15 cm to 30 cm. Diameter: About 4 mm to 6 mm. Texture, upper and lower surfaces: Pubescent; hairs orientated upright from petiole axis. Color, upper and lower surfaces: Close to 145A.

*Stipules*.—Length: Medium. Color: Light green becoming darker green with development.

Flower description:

*Flower form and flowering habit*.—Rotate flowers arranged singly at lateral apices; flowers held upright and at or below the foliar plane; flowers are self-fertile; about 22 to 27 flowers develop per plant.

*Fragrance*.—None detected.

*Natural flowering season*.—Early flowering habit; in the greenhouse, plants flower in late February into March and in outdoor production, plants flower in late April/early May in The Netherlands.

*Flower diameter*.—About 2.5 cm to 4 cm.

*Flower depth* (*height*).—About 4 mm to 8 mm.

*Petals*.—Arrangement: Single whorl of six petals; petals separate and not imbricate. Length: About 6 mm to 10 mm. Width: About 8 mm to 12 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D; color does not change with subsequent development. When opening and fully opened, lower surface: Close to 155D; color does not change with subsequent development.

*Sepals*.—Arrangement and calyx description: Single whorl of ten to twelve sepals; calyx, star-shaped; calyx adherence is strong and inserted; sepals are orientated upright; calyx diameter is smaller than fruit diameter. Calyx length: About 1.5 cm to 2 cm. Calyx diameter: About 2 cm to 3 cm. Shape: Lanceolate to ovate. Apex: Acute. Base: Fused. Margin: Entire. Texture, upper and lower surfaces: Pubescent. Color, upper and lower surfaces: Close to 137A.

*Peduncles*.—Length: About 3 cm to 12 cm. Diameter: About 1 mm to 3 mm. Strength: Strong. Texture: Pubescent; hairs orientated upright from pedicel axis. Color: Close to 144B.

*Reproductive organs*.—Stamens: Quantity per flower: About 25 to 30. Anther length: About 2 mm. Anther shape: Lanceolate to elliptic. Anther color: Close to 4B. Pollen amount: Abundant. Pollen color: Close to 12B. Pistils: Quantity per flower: About 30. Pistil length: About 1 mm to 2 mm. Stigma shape: Rounded. Stigma color: Close to 5A. Fruits: Quantity per truss: About five to ten; fruits are relatively large. Time to harvest: Early fruit ripening, fruits; fruits are ready to harvest in April to early May on plants grown under greenhouse conditions; fruit bearing is non-remontant. Postharvest longevity: About ten days at 7° C. Length: About 2 cm to 5 cm. Diameter: About 3 cm to 5 cm. Shape: Conical. Fruit weight per fruit, first quality: About 23.8 g. Fruit weight per plant, first quality: About 470 g. Firmness: Firm. Fragrance, taste: Pleasant; good balance between sweetness and acidity; nice aroma. Degrees brix: About 8.8 under greenhouse production conditions. Luster: Uniformly glossy. Surface unevenness: Mostly smooth; primary fruits are slightly more grooved than secondary fruits. Color, surface: Close to 40A. Color, flesh: Close to 35B; towards the center, close to 155C and center, close to 35B. Achene quantity: About 200 to 300 per fruit. Achene position: Level to slightly above the fruit surface. Achene weight: About 0.0005 g to 0.0006 g. Achene color: Close to 1B. Band width without achenes: Narrow, barely visible. Depth of core cavity: Small to medium.

Pathogen and pest resistance: Plants of the new Strawberry have been observed to be resistant to *Phytophthora cactorum, Sphaerotheca macularis* and *Verticillium dahliae*. To date, plants of the new Strawberry have not been observed to be resistant to pests and other pathogens common to Strawberry plants.

It is claimed:

1. A new and distinct Strawberry plant named 'Twist' as illustrated and described.

* * * * *